United States Patent [19]
Weder et al.

[11] Patent Number: 5,726,164
[45] Date of Patent: Mar. 10, 1998

[54] NANOSUSPENSIONS FOR INTRAVENOUS ADMINISTRATION

[75] Inventors: Hans Georg Weder, Rüschlikon; Peter van Hoogevest, Riehen, both of Switzerland

[73] Assignee: Novartis Corporation, Summit, N.J.

[21] Appl. No.: 619,068

[22] Filed: Mar. 20, 1996

[30] Foreign Application Priority Data

Mar. 21, 1995 [CH] Switzerland .......... 00804/95

[51] Int. Cl.$^6$ .......... A61K 31/35; A61K 31/55; A61K 31/40

[52] U.S. Cl. .......... 514/80; 514/103

[58] Field of Search .......... 514/103, 80

[56] References Cited

U.S. PATENT DOCUMENTS 5,093,330  3/1992  Caravatti et al. .......... 514/211

OTHER PUBLICATIONS

Wade et al, Handbook of Pharmaceutical Excipients Sec. Ed., The Pharmaceutical Press London, 1994, pp. 352–354.

*Primary Examiner*—C. Warren Ivy
*Assistant Examiner*—D.Margaret M. Mach
*Attorney, Agent, or Firm*—Marla J. Mathias; Gregory D. Ferraro

[57] ABSTRACT

The present invention relates to a pharmaceutical composition for the intravenous administration of the sparingly soluble staurosporin derivative N-benzoyl-staurosporin. The composition comprises the following preferred components:

a) the therpeutic agent N-benzoyl-staurosporin;

b) a polyoxyethylene/polyoxypropylene block copolymer;

c) ethanol and water as carrier liquids; and d) purified lecithin from soybeans and e) as water-soluble excipients glycerol and sorbitol.

11 Claims, No Drawings

NANOSUSPENSIONS FOR INTRAVENOUS ADMINISTRATION

The present invention relates to a pharmaceutical composition for the intravenous administration of a sparingly soluble staurosporin derivative, to a process for the preparation of said composition and to the use thereof in therapy.

The starting material for numerous derivatives, staurosporin, was isolated in 1977 from cultures of *Streptomyces staurosporeus* AWAYA, TAKAHASHI, OMURA SP. NOV. AM 2282, see S. Omura et al., J. Ant. 30, 275–281 (1977). Initially the relative configuration of the skeletal structure and later the absolute configuration was determined, see N. Fumato et al., Tetrahedron Letters 35: 8, 1251–1254 (1994). The following structural formula is assigned to the especially preferred N-benzoyl-staurosporin derivative, which is described in U.S. Pat. No. 5,093,330:

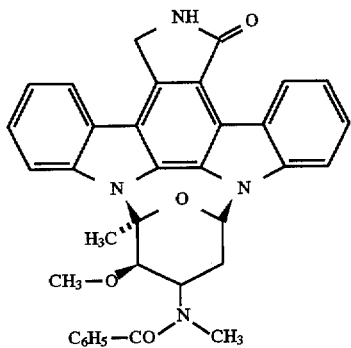

Staurosporin and its derivatives, such as N-benzoyl-staurosporin, effect a strong inhibition of protein kinase C, but they also inhibit other types of protein kinases. They are therapeutically applicable for various indications, especially as tumour inhibitors, as antiinflammatory agents, as antibiotics, and in the treatment of arteriosclerosis and of various diseases of the cardiovascular system and the central nervous system. A characteristic but undesirable property of staurosporin and most derivatives thereof is their extremely low water solubility, which has hitherto rendered their use for intravenous dosage forms very difficult.

Although peroral dosage forms, such as tablets or capsules, are gaining increasing importance, intravenous dosage forms continue to be relevant in spite of certain disadvantages. The disadvantages, which include administration only by a physician or specially authorized paramedical personnel and the special skills required of the person administering the drug, the "psychological" problems of the patient and his sensitivity to pain, and the complicated and expensive manufacture of those dosage forms, are offset by clear advantages. In the case of direct intravenous administration of a therapeutic agent, the metabolism in the gastrointestinal tract to which orally administered therapeutic agents are always subjected, can be substantially avoided. In particular, the so-called "first-pass effect" as a result of passage through the liver is minimised. Some therapeutic agents, which would be insufficiently capable of oral absorption, can only be administered by the intravenous route. Other therapeutic agents can be administered intravenously in a less efficacious dose than is required for oral administration. Generally, in the case of life-threatening diseases, such as tumour diseases, intravenous administration is preferred, as the problem of absorption through the gastrointestinal tract in conjunction with undesired metabolism is not acceptable.

A suitable intravenous dosage form has not yet been available for the important group of therapeutic agents consisting of staurosporins and staurosporin derivatives. It is the object of the present invention to make available a suitable intravenous dosage form for staurosporin derivatives, especially N-benzoyl-staurosporin.

Numerous publications propose various means of converting a sparingly soluble therapeutic agent into a more soluble form that is suitable for intravenous formulations. Such a conversion can be carried out, for example, with the aid of so-called solubilisers, such as 1,2-propylene glycol or polyethylene glycol 300–400. Where lack of solubility remains a problem which is not overcome in spite of the use of the few solubilisers permitted in national pharmacopoeias, finely dispersed systems based on lipid mixtures are proposed in the prior art. In such systems, the sparingly soluble therapeutic agent is encapsulated in lipid particles of a particle size of less than 1 μm and, together with the aqueous carrier liquid, forms a colloidally-dispersed or preferably finely dispersed system which, although it is not a true molecularly dispersed solution, is nevertheless sufficiently homogeneous for an intravenous dosage form. Numerous publications propose the encapsulation of sparingly soluble therapeutic agents in micelles, mixed micelles, inverse micelles or unilamellar or multilamellar liposomes.

These methods of manufacture have the definite advantage that they are useful for converting into intravenous dosage forms even therapeutic agents having a distinctly poor water solubility. However, they have the disadvantage of frequently encountered problems, such as inadequate stability of the dispersion, insufficient amounts of the therapeutic agent encapsulated, a high degree of dependence of the particle size on the process conditions, non-uniform process products obtained, inadequate reproducibility etc. From the technical standpoint the preparation of these systems is relatively complex in comparison with conventional mixing procedures: there are used, for example, high-pressure homogenisation, extrusion techniques, treatment with ultrasonic radiation etc. and corresponding apparatus technology. In addition, subsequent separating procedures, for example dialysis techniques, gel filtration or sterile filtration, are generally required before such dispersions can be administered.

Surprisingly, it has now been found that staurosporin, which has a particularly poor water solubility, and its derivatives are capable of forming finely dispersed systems having the homogeneity and stability necessary for intravenous dosage forms. This is achieved by using simple conventional mixing procedures provided that a polyoxyethylene/polyoxypropylene block copolymer and, optionally, additional pharmaceutically acceptable excipients are added.

The present invention relates to a pharmaceutical composition for the intravenous administration of staurosporin derivatives, which composition comprises:

a) a staurosporin derivative which is sparingly soluble in water;

b) a polyoxyethylene/polyoxypropylene block copolymer;

c) ethanol and water as carrier liquids in the degree of purity prescribed for intravenous administration; and, optionally, d) a phospholipid of the formula

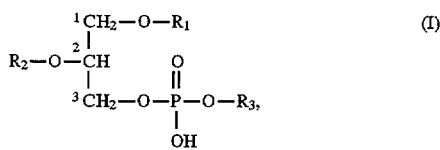

wherein $R_1$ is $C_{10-20}$acyl; $R_2$ is hydrogen or $C_{10-20}$acyl; $R_3$ is hydrogen, 2-trimethylamino-1-ethyl, 2-amino-1-ethyl, $C_{1-4}$alkyl, $C_{1-5}$alkyl substituted by carboxy, $C_{2-5}$alkyl substituted by hydroxy, $C_{2-5}$alkyl substituted by carboxy and hydroxy, $C_{2-5}$alkyl substituted by carboxy and amino, or an inositol group or a glyceryl group, or a salt of such a compound; and/or e) water-soluble excipients suitable for injections.

The pharmaceutical composition defined above is distinguished by useful phase properties of the solubilised therapeutic agent. For example, where opalescence and transparency occur in incident light, only an extremely slight milky turbidity reveals that the dispersion formed still has physical differences vis-è-vis the ideal state of a true molecular solution. Electron microscope images show that a population of more than 95% of the sparingly soluble active ingredient is present in the form of a suspension of particles having a particle size of approximately 5–20 nm ("nanosuspension"). However, these differences vis-à-vis a true solution are acceptable in view of the particularly good homogeneity properties of the dispersion. These properties can be made apparent in a high storage stability; for example there is no separation after storage for several months at 2°–8° C. (by extrapolation the expected stability is more than two years).

An especially preferred embodiment of this invention relates to a pharmaceutical composition comprising:

a) the therapeutic agent N-benzoyl-staurosporin;
b) a polyoxyethylene/polyoxypropylene block copolymer;
c) ethanol and water as carrier liquids; and
d) purified lecithin from soybeans; and
e) as water-soluble excipients glycerol and sorbitol.

A further preferred embodiment of this invention relates to a pharmaceutical composition comprising:

a) the therapeutic agent N-benzoyl-staurosporin;
b) a polyoxyethylene/polyoxypropylene block copolymer;
c) ethanol and water as carrier liquids; and
e) as water-soluble excipient glycerol.

A very especially preferred embodiment of this invention relates to a pharmaceutical composition comprising:

a) the therapeutic agent N-benzoyl-staurosporin;
b) poloxamer 188;
c) ethanol and water as carrier liquids; and
d) purified lecithin from soybeans; and
e) as water-soluble excipients glycerol and sorbitol.

A further very especially preferred embodiment of this invention relates to a pharmaceutical composition comprising:

a) the therapeutic agent N-benzoyl-staurosporin;
b) poloxamer 188;
c) ethanol and water as carrier liquids; and
e) as water-soluble excipient glycerol.

Component a)

A staurosporin derivative that is sparingly soluble in water is disclosed, for example, in U.S. Pat. No. 5,093,330 and is derived from staurosporin by additional substitution of the free hydrogen atom at the nitrogen of the N-methylamino substituent. Poor solubility in water is a characteristic property of staurosporin derivatives, which renders them unsuitable for intravenous dosage forms. For example, N-benzoyl-staurosporin, which is especially effective, has the low water-solubility of less than 0.1 mg/litre at room temperature.

Suitable staurosporin derivatives are, for example, N-(3-nitrobenzoyl)-staurosporin, N-(3-fluorobenzoyl)-staurosporin, N-trifluoroacetyl-staurosporin, N-phenylcarbamoyl-staurosporin, N-(3-carboxypropionyl)-staurosporin, N-methylaminothiocarbonyl-staurosporin, N-tert-butoxycarbonyl-staurosporin, N-(4-carboxybenzoyl)-staurosporin, N-(3,5-dinitrobenzoyl)-staurosporin, N-(2-aminoacetyl)-staurosporin, N-alanylstaurosporin and pharmaceutically acceptable salts of those derivatives. The N-benzoylstauresporin derivative is especially preferred.

Component b)

The polyoxyethylene/polyoxypropylene block copolymer is also known as "poloxamer", see the corresponding entry in "Hagers Handbuch der Pharmazeutischen Praxis", 5th Edition. That block copolymer is a block copolymer of ethylene oxide and propylene oxide which is commercially available and has molecular weights of approximately from 100 to 16000. The degree of polymerisation of the ethylene oxide units therein is about 10 to 110 and of the propylene oxide units about 20 to 60. Suitable types are mainly those referred to as poloxamer 124, 188, 237, 338 and 407 in USP XXII.

An especially preferred polyoxyethylene/polyoxypropylene block copolymer is known by the name poloxamer 188 and is commercially available (BASF) under the names Pluronic® F68 and Lutrol® F68.

Component c)

The carrier liquid ethanol is present in the degree of purity (96%) prescribed for injection formulations in accordance with the regulations of the national pharmacopoeias, such as The U.S. Pharmacopoeia (USP) or the Deutsches Arzneibuch (DAB). The proportion of ethanol can vary within wide limits from approximately 1% to approximately 50%, preferably from approximately 1% to approximately 10%. The second carrier liquid, water, has the degree of purity prescribed for intravenous administration and is germ- and pyrogen-free in accordance with the regulations of the national pharmacopoeias.

Component d)

The nomenclature used for the phospholipids (I) and the numbering of the carbon atoms (sn-nomenclature, stereospecific numbering) are in accordance with the recommendations made by the IUPAC-IUB Commission on Biochemical Nomenclature (CBN) in Eur. J. of Biochem. 79, 11–21 (1977) "Nomenclature of Lipida".

$R_1$ and $R_2$ defined as $C_{10-20}$acyl are preferably straight-chain $C_{10-20}$alkanoyl having an even number of carbon atoms and straight-chain $C_{10-20}$alkenoyl having from one to three double bonds and an even number of carbon atoms.

Straight-chain $C_{10-20}$alkanoyl $R_1$ and $R_2$ having an even number of carbon atoms are, for example, n-dodecanoyl, n-tetradecanoyl, n-hexadecanoyl or n-octadecanoyl.

Straight-chain $C_{10-20}$alkenoyl $R_1$ and $R_2$ having from one to three double bonds and an even number of carbon atoms are, for example, 6-cis-, 6-trans-, 9-cis- or 9-trans-dodecenoyl, -tetradecenoyl, -hexadecenoyl, -octadecenoyl or -icosenoyl, especially 9-cis-octadecenoyl (oleoyl), and also 9,12-cis-octadecadienoyl or 9,12,15-cis-octadecatrienoyl.

A phospholipid (I), wherein $R_3$ is 2-trimethylamino-1-ethyl, is referred to by the trivial name lecithin and a phospholipid (I), wherein $R_3$ is 2-amino-1-ethyl, by the trivial name cephalin. Suitable are, for example, naturally occurring cephalin or lecithin, for example cephalin or lecithin from soybeans or chicken eggs having different or identical acyl groups $R_1$ and $R_2$, or mixtures thereof.

However, the phospholipid (I) may also be of synthetic origin. The expression "synthetic phospholipid" is used to define phospholipids having a uniform composition in respect of $R_1$ and $R_2$. Such synthetic phospholipids are preferably the above-defined lecithins and cephalins, wherein the acyl groups $R_1$ and $R_2$ have a defined structure and are derived from a defined fatty acid having a degree of purity greater than approximately 95%. $R_1$ and $R_2$ may be identical or different and unsaturated or saturated. Preferably, $R_1$ is saturated, for example n-hexadecanoyl, and $R_2$ is unsaturated, for example 9-cis-octadecenoyl (=oleoyl).

The expression "naturally occurring" defines a phospholipid (I) that does not have a uniform composition in respect of $R_1$ and $R_2$. Such natural phospholipids are likewise lecithins and cephalins, wherein the acyl groups $R_1$ and $R_2$ are structurally undefinable and are derived from naturally occurring fatty acid mixtures.

The requirement "substantially pure" defines a phospholipid (I) having a degree of purity of more than 90% (by weight), preferably more than 95%, which can be demonstrated by means of suitable determination methods, for example by paper chromatography, by thin-layer chromatography, by HPLC or by means of enzymatic colour testing.

In a phospholipid (I), $R_3$ defined as $C_{1-4}$alkyl is, for example, methyl or ethyl. Methyl is preferred.

$R_3$ defined as $C_{1-5}$-alkyl substituted by carboxy, $C_{2-5}$-alkyl substituted by hydroxy or $C_{2-5}$alkyl substituted by carboxy or hydroxy is, for example, 2-hydroxyethyl, 2,3-dihydroxy-n-propyl, carboxymethyl, 1- or 2-carboxyethyl, dicarboxymethyl, 2-carboxy-2-hydroxyethyl or 3-carboxy-2,3-dihydroxy-n-propyl.

$R_3$ defined as $C_{2-5}$alkyl substituted by carboxy and amino is, for example, 3-amino-3-carboxy-n-propyl or 2-amino-2-carboxy-n-propyl, preferably 2-amino-2-carboxyethyl. A phospholipid (I) having those groups may be in salt form, for example in sodium or potassium salt form.

Phospholipids (I) wherein $R_3$ is the inositol or the glyceryl group are known by the names phosphatidylinositol and phosphatidylglycerol.

The acyl radicals in the phospholipids (I) are also customarily known by the names given in brackets:

9-cis-Dodecenoyl (lauroleoyl), 9-cis-tetradecenoyl (myristoleoyl), 9-cis-hexadecenoyl (palmitoleoyl), 6-cis-octadecenoyl (petroseloyl), 6-trans-octadecenoyl (petroselaidoyl), 9-cis-octadecenoyl (oleoyl), 9-trans-octadecenoyl (elaidoyl), 11-cis-octadecenoyl (vaccenoyl), 9-cis-icosenoyl (gadoleoyl), n-dodecanoyl (lauroyl), n-tetradecanoyl (myristoyl), n-hexadecanoyl (palmitoyl), n-octadecanoyl (stearoyl), n-icosanoyl (arachidoyl), n-docosanoyl (behenoyl), n-tetracosanoyl (lignoceroyl).

A salt of the phospholipid (I) is pharmaceutically acceptable. Salts are defined by the existence of salt-forming groups in the substituent $R_3$ and by the free hydroxy group at the phosphorus atom. The formation of internal salts is also possible. Alkali metal salts, especially the sodium salt, are preferred.

In an especially preferred embodiment of this invention, purified lecithin from soybeans, for example of the LIPOID S 100 type, is used.
Component e)

If desired, water-soluble excipients suitable for injections may be present in the pharmaceutical composition. Anhydrous glycerol is especially preferred. The compositions may also comprise excipients for the establishment of isotonic conditions, for example ionic excipients, for example sodium chloride, or other water-soluble excipients of pharmaceutically acceptable hexose types, for example sorbitol, mannitol, glucose, lactose or sorbitan.

In a preferred embodiment of this invention, anhydrous glycerol and, in addition, sorbitol are present.

The invention relates also to the process known per se for the preparation of the pharmaceutical composition, which process comprises preparing an aqueous dispersion by homogeneously mixing components a), b) and c) and optionally d) and/or e) and subjecting the dispersion obtainable to the following subsequent operations:

α) addition of a further amount of water as carrier liquid and optionally further water-soluble excipients that are suitable for injections; filtration and optionally dialysis of the clear dispersion; or β) filtration and optionally dialysis and subsequent conversion of the dispersion obtainable into a dry preparation, optionally with the addition of water-soluble excipients, and reconstitution of the dry preparation to form an injectable dispersion.

In an especially preferred embodiment of the process, an intravenously administrable dispersion having nanoparticles of the sparingly water-soluble staurosporin derivative N-benzoyl-staurosporin is prepared.

In another especially preferred embodiment of the process there is used as the formulation base the polyoxyethylene/polyoxypropylene block copolymer of component b), combined with a phospholipid of formula I (component d)), and glycerol and a pharmaceutically acceptable hexose, for example sorbitol, are added as water-soluble excipients of component e) to the carrier liquids ethanol and water (component c)).

A formulation base that can be used for the preferred embodiment of the process, comprising b) a polyoxyethylene/polyoxypropylene block copolymer;

c) ethanol and water as carrier liquids; and d) a phospholipid of the formula

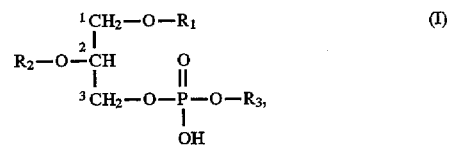

wherein $R_1$, $R_2$ and $R_3$ are as defined above; and optionally e) as water-soluble excipients glycerol and/or a pharmaceutically acceptable hexose, is novel and is also a subject of the present invention.

That formulation base is suitable both for intravenous dosage forms and for those dosage forms in which the solubilisation of a sparingly soluble active ingredient is necessary, for example capsule fillings, drops, lotions or emulsions for ointments, gels, creams etc. To the latter there may also be added the other excipients typical of such dosage forms. The formulation base can be used both for solubilising sparingly soluble staurosporin derivatives in accordance with the stated object of this invention and for solubilising other sparingly soluble active ingredients.

Special preference is given to the formulation base comprising b) a polyoxyethylene/polyoxypropylene block copolymer;

c) ethanol and water as carrier liquids; and d) purified lecithin from soybeans; and optionally e) as water-soluble excipient(s) glycerol and/or sorbitol.

In accordance with an especially preferred process variant, an intravenously administrable dispersion containing nanoparticles of the sparingly water-soluble staurosporin derivative N-benzoyl-staurosporin and having the following formulation base is prepared:

b) poloxamer 188;
c) ethanol and water as carrier liquids;
d) purified lecithin from soybeans; and
e) as water-soluble excipients glycerol and sorbitol.

For the preparation of that dispersion, the lecithin from soybeans is placed in ethanol, then the active ingredient N-benzoyl-staurosporin is slowly added thereto followed by glycerol and a concentrated aqueous solution of sorbitol. The mixture is made up to the volume required for injection or infusion solutions with water (aqua ad inj.).

Mixing can be effected by vigorous shaking using a dispersing machine, for example a Vortex mixer, or using dispersing machines of the POLYTRON type (Kinematica AG, Littau Switzerland) or dispersing machines produced by IKA (Staufen, Germany), a static mixer and conventional stirring machines having a propeller or paddle blade or using a magnetic stirrer or phase mixer. In order to obtain an especially homogeneous mixture, stirring is carried out at high speed, for example using stirring machines produced by Polytron, for example Polytron PT 3000 or DH 30/30. Approximately from 0.1 to 50% by weight of the constituents (without the water component), based on the total weight of the suspension, preferably approximately from 2 to 20% by weight, can be dispersed in the aqueous phase. When phospholipids are used (component d)), observation of the so-called phase transition temperature (gel-form/liquid crystalline) of the phospholipids used is critical. Dispersion is preferably effected at temperatures at which the phospholipid used is present in the liquid-crystalline state, that is to say above the so-called phase transition temperature. A phospholipid that is in the liquid crystalline state at room temperature or lower temperatures, for example lecithin from soybeans, is especially suitable.

The mixture obtainable can be defined as a suspension of colloidal nanoparticles of the sparingly soluble staurosporin derivative or, more simply, as a nanosuspension. By means of measurements from laser light scattering and electron micrographs, the colloidal particles present in the suspension can be distinguished from other particles such as liquid crystals, micelles, inverse micelles or liposomes. For the statistical plurality of more than 90%, especially more than 95%, an average particle size of less than 20 nm is typical.

For the identification of the nanosuspensions obtainable, methods known per se are suitable, for example optical examination: a slight to intense opalescence of the preparation is easily identifiable (indicates average particle size of less than 20 nm); laser light scattering (determination of the particle size and homogeneity); or electron microscopy (freeze fracture and negative contrast technique). Subsequent operations)

The necessary amount of water, which must be of the purity prescribed for injectables, can be added to the nanosuspension. This nanosuspension can be directly administered after selecting the filtration method suitable for such types of dispersions, for example sterile gel filtration, for example using Sepharose® or Sephacryl® (Pharmacia) as carrier, or preferably sterile filtration (0.2 µm), for example with a PAL filter (Gelman), and optionally after adding further water-soluble excipients that can be used for intravenous dosage forms. Especially sterile-filtration is applicable to separate off all the relatively large particles in the dispersion having a diameter greater than about 200 nm, as well as floating and solid substances, and excess, dispersed lipids which may be present in high-molecular-weight aggregates. This yields a nanosuspension having a high proportion of hydrophilic particles of relatively uniform size. Alternatively or in addition to sterile filtration, the nanosuspension can be subjected to dialysis and/or ultrafiltration for the purpose of purification.

As an alternative to the preparation of a directly administrable nanosuspension, the subsequent purification steps described above may be carried out and the purified nanosuspension may be converted into a dry preparation, especially into a lyophilisate, which is reconstituted prior to administration by the addition of water. An administrable nanosuspension is obtained again after reconstitution of the lyophilisate. For the preparation of lyophilisates, the addition of so-called builders, such as lactose or mannitol, is customary. These excipients are added in such amounts that after reconstitution of the lyophilisate the nanosuspension to be administered has isotonic properties.

Measured amounts of nanosuspension are introduced, optionally in the form of a concentrate, into containers suitable for a unit dose, for example glass ampoules (vials). The filled containers can be cooled, if desired, to about –40° to –50° C., especially to about –45° C., and then lyophilised at a pressure of about 0.2 to 0.6 mbar by slowly heating to a final temperature of about 25° to 35° C.

The pharmaceutical compositions described hereinbefore can be used as intravenously administrable medicaments for the treatment of diseases that are caused by malignant cell growth. They are especially suitable as tumour inhibitors, as antiinflammatories, as antibiotics, in the treatment of arteriosclerosis or they can be used therapeutically in various disorders of the cardiovascular system and the central nervous system.

The following Examples illustrate the invention.

EXAMPLE 1

Formulation for 20 injection formulations, each of 5 ml and comprising 100 mg of active ingredient:

| | |
|---|---|
| 2.0 g | N-benzoyl-staurosporin |
| 10.0 g | LUTROL F68 |
| 2.0 g | lecithin from soybean oil (LIPOID S 100) |
| 30.0 g | glycerol (anhydrous) |
| 21.0 g | sorbitol solution 70% (w/w) |
| 35.0 g | ethanol (abs. 96%) |
| 100.0 g | batch |

The LIPOID S 100 is dissolved in ethanol and stirred with a magnetic stirrer at room temperature. LUTROL F68 is added and the mixture is stirred at about 35° C. The active ingredient, N-benzoyl-staurosporin, is added to the batch and stirring is continued for 10 minutes, likewise at 35° C. The glycerol is then mixed in and stirring is continued at room temperature until the mixture becomes clear. The 70% sorbitol solution, which has been prepared beforehand by dissolving sorbitol in water, is then added. The mixture is again stirred using the magnetic stirrer until the mixture becomes clear. The mixture is then sterile-filtered (pore filter: 0.2 µm) and introduced into containers under sterile conditions. The formulations are then stored at 4°–7° C.

EXAMPLE 2

Preparation of an infusion solution

The batch according to Example 1 can also be used for the preparation of infusion solutions of 250 ml volume: 235 g of 5% glucose solution or 0.9% NaCl solution are prepared at room temperature and 15 ml of the solution prepared according to Example 1 are added. The infusion solution is then sterile-filtered (pore filter: 0.2 μm) and introduced into containers under sterile conditions. The infusion solution has the following concentrations:

| | |
|---|---|
| 0.12% | N-benzoyl-staurosporin |
| 0.60% | LUTROL F68 |
| 0.12% | lecithin from soybean oil (LIPOID S 100) |
| 1.80% | glycerol (anhydrous) |
| 0.88% | sorbitol solution 70% (w/w) |
| 2.10% | ethanol (abs. 96%) |

EXAMPLE 3

Preparation of an infusion formulation

A solution consisting of 600 mg of LUTROL F68, 1200 mg of ethanol and 2500 mg of glycerol is prepared and 1500 mg of N-benzoyl-staurosporin are added thereto. The mixture is then supplied to a static mixer (three SMX elements having a diameter of 3.2 mm) at a pump speed of 0.5–7.5 ml/min. 95.55 g of an aqueous solution containing 0.9% NaCl or 5% glucose, sorbitol or mannitol are then mixed in, the solution being added at a pump speed of from 50 to 75 ml/min. The infusion solution contains the following constituents per ml:

| | |
|---|---|
| 1.5 mg | N-benzoyl-staurosporin |
| 6.0 mg | LUTROL F68 |
| 12.0 mg | ethanol |
| 25.0 mg | glycerol |

What is claimed is:

1. A pharmaceutical composition for the intravenous administration of a staurosporin derivative comprising
   a) a staurosporin derivative which is sparingly soluble in water;
   b) a polyoxyethylene/polyoxypropylene block copolymer;
   c) ethanol and water as carrier liquids in the degree of purity prescribed for intravenous administration; and optionally
   d) a phospholipid of the formula

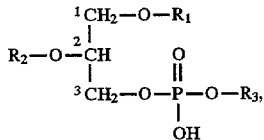

$$\begin{array}{c} {}^1CH_2-O-R_1 \\ {}^2| \\ R_2-O-CH \quad O \\ | \quad \parallel \\ {}^3CH_2-O-P-O-R_3, \\ | \\ OH \end{array} \quad (I)$$

wherein $R_1$ is $C_{10-20}$acyl; $R_2$ is hydrogen or $C_{10-20}$acyl; $R_3$ is hydrogen, 2-trimethylamino-1-ethyl, 2-amino-1-ethyl, $C_{1-4}$alkyl, $C_{1-5}$alkyl substituted by carboxy, $C_{2-5}$alkyl substituted by hydroxy, $C_{2-5}$alkyl substituted by carboxy and hydroxy, $C_{2-5}$alkyl substituted by carboxy and amino, or an inositol or a glyceryl group, or a salt of such a compound; and/or
   e) water-soluble excipients suitable for injections.

2. A pharmaceutical composition according to claim 1 comprising:
   a) the therapeutic agent N-benzoyl-staurosporin;
   b) a polyoxyethylene/polyoxypropylene block copolymer;
   c) ethanol and water as carrier liquids;
   d) purified lecithin from soybeans; and
   e) glycerol and sorbitol as water-soluble excipients.

3. A pharmaceutical composition according to claim 1 comprising:
   a) the therapeutic agent N-benzoyl-staurosporin;
   b) a polyoxyethylene/polyoxypropylene block copolymer;
   c) ethanol and water as carrier liquids; and
   e) glycerol as water-soluble excipient.

4. A pharmaceutical composition according to claim 2 comprising:
   a) the therapeutic agent N-benzoyl-staurosporin;
   b) polyoxyethylene/polyoxypropylene block copolymer;
   c) ethanol and water as carrier liquids;
   d) purified lecithin from soybeans; and
   e) glycerol and sorbitol as water-soluble excipients.

5. A pharmaceutical composition according to claim 3 comprising:
   a) the therapeutic agent N-benzoyl-staurosporin;
   b) ethyleneglycol-propylene glycol block copolymer;
   c) ethanol and water as carrier liquids; and
   e) glycerol as water-soluble excipient.

6. A process for the preparation of a pharmaceutical composition according to claim 1, which process comprises preparing an aqueous dispersion by homogeneously mixing components a), b) and c) and optionally d) and/or e) and subjecting the dispersion obtainable to the following subsequent operations:
   α) addition of a further amount of water as carrier liquid and optionally further water-soluble excipients that are suitable for injections; filtration and optionally dialysis of the clear dispersion; or
   β) filtration and optionally dialysis and subsequent conversion of the dispersion obtainable into a dry preparation, optionally with the addition of water-soluble excipients, and reconstitution of the dry preparation to form an injectable dispersion.

7. A process according to claim 6, which comprises preparing an intravenously administrable dispersion containing nanoparticles of the sparingly water-soluble staurosporin derivative N-benzoyl-staurosporin.

8. A nanosuspension obtainable by preparing an aqueous dispersion by homogeneously mixing components a), b), and c) and optionally d) and/or e) of claim 1 and subjecting the dispersion obtainable to the following subsequent operations:
   α) addition of a further amount of water as carrier liquid and optionally further water-soluble excipients that are suitable for injection; filtration and optionally dialysis of the clear dispersion; or
   β) filtration and optionally dialysis and subsequent conversion of the dispersion obtainable into a dry preparation, optionally with the addition of water-soluble excipients, and reconstitution of the dry preparation to form an injectable dispersion, wherein said nanosuspension comprises a sparingly water-soluble staurosporin derivative.

9. The nanosuspension of claim 8, comprising N-benzoyl-staurosporin.

10. A concentrate or dry preparation obtainable by preparing an aqueous dispersion by homogeneously mixing components a), b), and c) and optionally d) and/or e) of claim 1 and subjecting the dispersion obtainable to the following subsequent operations:

α) addition of a further amount of water as carrier liquid and optionally further water-soluble excipients that are suitable for injection; filtration and optionally dialysis of the clear dispersion; or β) filtration and optionally dialysis and subsequent conversion of the dispersion obtainable into a dry preparation, optionally with the addition of water-soluble excipients, and reconstitution of the dry preparation to form an injectable dispersion.

11. A method of treating a tumor comprising administering a therapeutically effective amount of a nanosuspension comprising N-benzoyl-staurosporin to a patient in need thereof.

* * * * *